(12) United States Patent
Carballo

(10) Patent No.: US 10,485,250 B2
(45) Date of Patent: Nov. 26, 2019

(54) PRODUCE DRAWER

(71) Applicant: Haier US Appliance Solutions, Inc., Wilmington, DE (US)

(72) Inventor: Daniel Carballo, Louisville, KY (US)

(73) Assignee: Haier US Appliance Solutions, Inc., Wilmington, DE (US)

(*) Notice: Subject to any disclaimer, the term of this patent is extended or adjusted under 35 U.S.C. 154(b) by 151 days.

(21) Appl. No.: 15/594,773

(22) Filed: May 15, 2017

(65) Prior Publication Data

US 2018/0325148 A1    Nov. 15, 2018

(51) Int. Cl.
*A23L 3/28* (2006.01)
*F25D 17/04* (2006.01)
*A23L 3/36* (2006.01)
*F25D 25/02* (2006.01)
*A61L 2/10* (2006.01)

(52) U.S. Cl.
CPC .......... *A23L 3/28* (2013.01); *A23L 3/36* (2013.01); *F25D 17/042* (2013.01); *F25D 25/025* (2013.01); *A61L 2/10* (2013.01)

(58) Field of Classification Search
CPC ............... F25D 25/025; F25D 17/042; F25D 2317/0417; A61L 2/10; A23L 3/28; A23L 3/26
See application file for complete search history.

(56) References Cited

U.S. PATENT DOCUMENTS

| 5,641,217 A * | 6/1997 | Caruso ................ F25D 25/025 312/334.23 |
| 5,901,564 A | 5/1999 | Comeau, II |
| 6,477,853 B1 | 11/2002 | Khorram |
| 8,979,621 B2 * | 3/2015 | Kelly .................. F25D 17/042 454/173 |
| 2014/0060104 A1 | 3/2014 | Shur |
| 2015/0165079 A1 * | 6/2015 | Shur ....................... A61L 2/10 250/455.11 |

FOREIGN PATENT DOCUMENTS

| CA | 2882208 A1 | 8/2016 |
| DE | 102013010620 A1 | 1/2015 |
| WO | WO2015005661 A1 | 1/2015 |
| WO | WO2015150091 A1 | 10/2015 |

* cited by examiner

*Primary Examiner* — Elizabeth J Martin
(74) *Attorney, Agent, or Firm* — Dority & Manning, P.A.

(57) ABSTRACT

A refrigerator appliance including a shelf and a removably mountable drawer assembly having housing and a drawer slidably mounted within the housing. The drawer assembly having a first rail on a first side of the housing and a second rail on a second side of the housing. The first rail and the second rail of the removably mountable drawer assembly are removably mounted to the shelf.

19 Claims, 6 Drawing Sheets

PRODUCE DRAWER

FIELD

The present disclosure is related generally to refrigerator appliances, and more particularly to systems and methods for storing and preserving produce in a refrigerator appliance.

BACKGROUND

Refrigerator appliances generally include a cabinet that defines a chilled chamber. A wide variety of food items may be stored within the chilled chamber. The low temperature of the chilled chamber relative to ambient atmosphere assists with increasing a shelf life of the food items stored within the chilled chamber.

However, various different food items may have differing storage requirements. For example, produce, e.g., fruits and vegetables, may last longer when stored with lighting conditions that are optimized for the particular needs of the fruits and/or vegetables.

Accordingly, a refrigerator with features for increasing the storage shelf life of produce items therein would be useful.

BRIEF DESCRIPTION

A refrigerator appliance includes a shelf and a removably mountable drawer assembly. The drawer assembly includes a housing and a drawer slidably mounted within the housing. The drawer defines a food storage compartment. The drawer assembly also includes a first rail on a first side of the housing and a second rail on a second side of the housing. The first rail and the second rail of the removably mountable drawer assembly are configured for removably mounting to the shelf. Additional aspects and advantages of the invention will be set forth in part in the following description, or may be apparent from the description, or may be learned through practice of the invention.

In a first exemplary embodiment, a refrigerator appliance is provided. The refrigerator appliance defines a vertical direction, a lateral direction, and a transverse direction, the vertical, lateral, and transverse directions being mutually perpendicular. The refrigerator appliance includes a cabinet defining a food storage chamber. The food storage chamber extends between a top portion and a bottom portion along the vertical direction, a first side portion and a second side portion along the lateral direction, and a front portion and a back portion along the transverse direction. A first support member and a second support member are disposed proximate the back portion of the food storage chamber for providing a plurality of shelf mounting positions. The first support member and the second support member each define a plurality of openings. The refrigerator appliance also includes a shelf having a first bracket and a second bracket attached to the shelf for mounting the shelf to the first and second support members in one of the shelf mounting positions and a removably mountable drawer assembly. The drawer assembly includes a housing comprising an exterior, an interior, and a chamber defined in the interior of the housing. The drawer assembly also includes a drawer slidably mounted within the chamber of the housing. The drawer defines a food storage compartment. A door is positioned at a front portion of the drawer. The door is configured to sealingly enclose the chamber of the housing when the drawer is in a closed position. The drawer assembly also includes a first rail that extends along the transverse direction on a first side of the exterior of housing and a second rail that extends along the transverse direction on a second side of the exterior of the housing. The second side is opposite the first side. The first rail and the second rail of the removably mountable drawer assembly are configured for removably mounting to the first bracket and the second bracket of the shelf proximate a bottom surface of the shelf.

In a second exemplary embodiment, a removably mountable drawer assembly for a refrigerator is provided. The drawer assembly includes a housing. The housing defines a vertical direction, a lateral direction, and a transverse direction. The vertical, lateral, and transverse directions are mutually perpendicular. The housing includes an exterior, an interior, and a chamber defined in the interior of the housing. The drawer assembly also includes a drawer slidably mounted within the chamber of the housing. The drawer defines a food storage compartment. A door is positioned at a front portion of the drawer. The door is configured to sealingly enclose the chamber of the housing when the drawer is in a closed position. The drawer assembly also includes a first rail that extends along the transverse direction on a first side of the exterior of housing and a second rail that extends along the transverse direction on a second side of the exterior of the housing. The second side is opposite the first side. The first rail and the second rail are configured for removably mounting to a first bracket and a second bracket of a shelf proximate a bottom surface of the shelf.

In a third exemplary embodiment, a method of extending the shelf life of produce stored in a drawer of a refrigerator is provided. The method includes operating a plurality of light-emitting diodes over a twenty-four hour cycle. The twenty-four hour cycle includes irradiating the produce within the drawer with a gradually increasing intensity of ultraviolet light for a first period of time. The twenty-four hour cycle also includes irradiating the produce within the drawer with a gradually decreasing intensity of ultraviolet light for a second period of time until the intensity of the ultraviolet light is about zero and keeping the intensity of the ultraviolet light at about zero for a third period of time. The first period of time, the second period of time, and the third period of time collectively define a twenty-four hour period. The method also includes repeating the twenty-four hour cycle.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
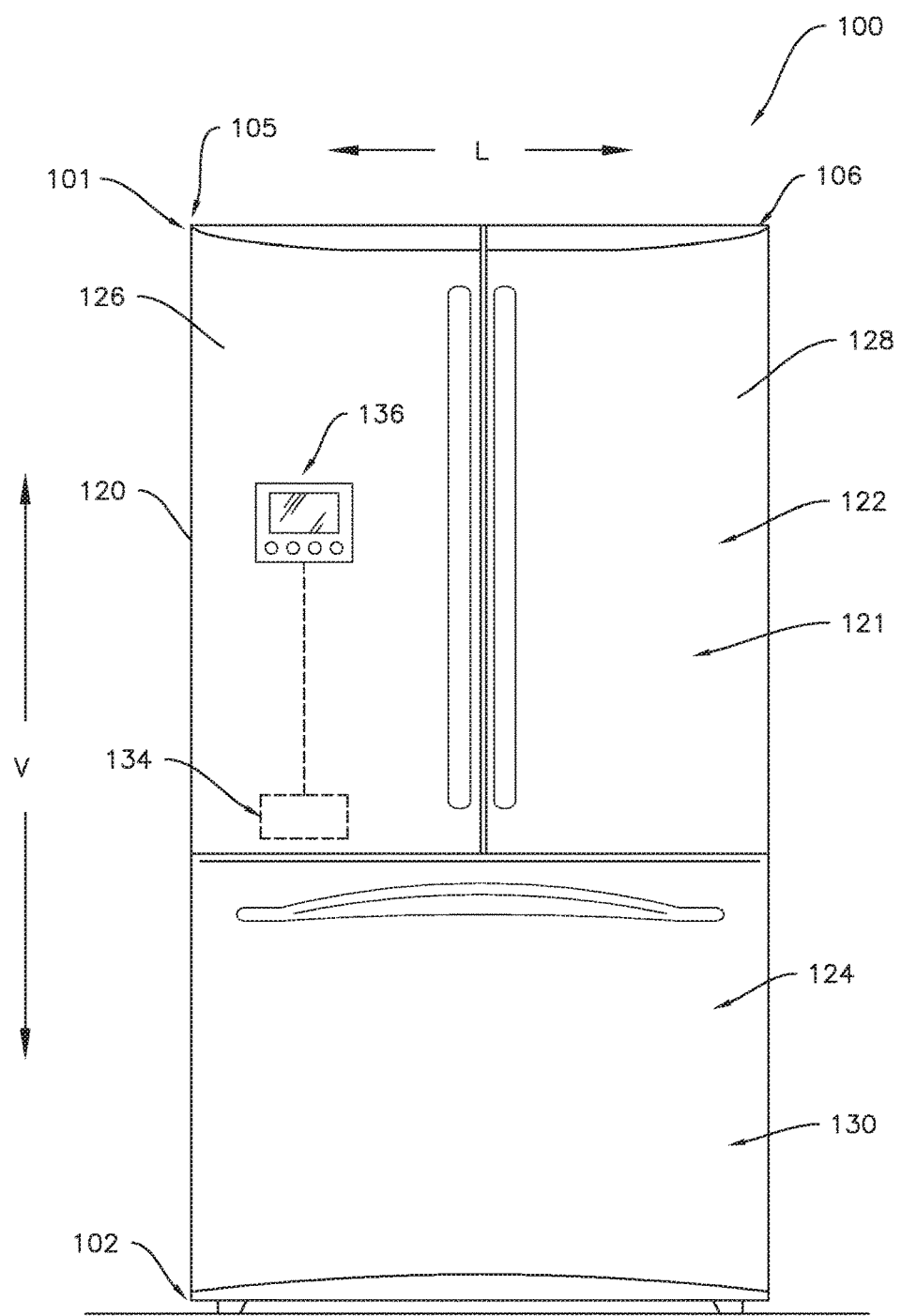
FIG. 1 provides a front view of a refrigerator appliance according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 provides a front view of a refrigerator appliance 100 according to an exemplary embodiment of the present subject matter. Refrigerator appliance 100 extends between a top portion 101 and a bottom portion 102 along a vertical direction V. Refrigerator appliance 100 also extends between a first side portion 105 and a second side portion 106 along a lateral direction L. A transverse direction T (FIG. 2) is defined perpendicular to the vertical and lateral directions V, L. Accordingly, vertical direction V, lateral direction L, and transverse direction T are mutually perpendicular.

Refrigerator appliance 100 includes a housing or cabinet 120 defining a volume 121 including at least one food storage chamber defined therein. In the illustrated example embodiment, cabinet 120 defines multiple food storage chambers, e.g., an upper fresh food chamber 122 and a lower freezer chamber 124 arranged below the fresh food chamber 122 on the vertical direction V. As such, refrigerator appliance 100 is generally referred to as a bottom mount refrigerator. In this exemplary embodiment, cabinet 120 also defines a mechanical compartment (not shown) for receipt of a sealed cooling system (not shown). It will be appreciated that the present subject matter can be used with other types of refrigerators (e.g., side-by-sides), freezer appliances, and/or other types of appliances more generally. Consequently, the description set forth herein is for exemplary purposes only and is not intended to limit the scope of the present subject matter in any aspect.

Refrigerator appliance 100 includes refrigerator doors 126, 128 that are rotatably hinged to an edge of cabinet 120 for accessing fresh food chamber 122. It should be noted that while doors 126, 128 are depicted in a "French door" configuration, any suitable arrangement or number of doors is within the scope and spirit of the present subject matter. A freezer door 130 is arranged below refrigerator doors 126, 128 for accessing freezer chamber 124.

Operation of refrigerator appliance 100 can be regulated by a controller 134 that is operatively coupled to a user interface panel 136. Panel 136 provides selections for user manipulation of the operation of refrigerator appliance 100. In response to user manipulation of user interface panel 136, controller 134 operates various components of refrigerator appliance 100. Controller 134 may include a memory and one or more processors, microprocessors, CPUs or the like, such as general or special purpose microprocessors operable to execute programming instructions or micro-control code associated with operation of refrigerator appliance 100. The memory may represent random access memory such as DRAM, or read only memory such as ROM or FLASH. In one embodiment, the processor executes programming instructions stored in memory. The memory may be a separate component from the processor or may be included onboard within the processor.

Controller 134 may be positioned in a variety of locations throughout refrigerator appliance 100. In the illustrated embodiment, controller 134 is located within door 126. In such an embodiment, input/output ("I/O") signals may be routed between the controller and various operational components of refrigerator appliance 100. In one embodiment, user interface panel 136 may represent a general purpose I/O ("GPIO") device or functional block. The user interface 136 may include input components, such as one or more of a variety of electrical, mechanical or electro-mechanical input devices including rotary dials, push buttons, and touch pads. User interface 136 may include a display component, such as a digital or analog display device designed to provide operational feedback to a user. The user interface 136 may be in communication with controller 134 via one or more signal lines or shared communication busses.

Figure 2:
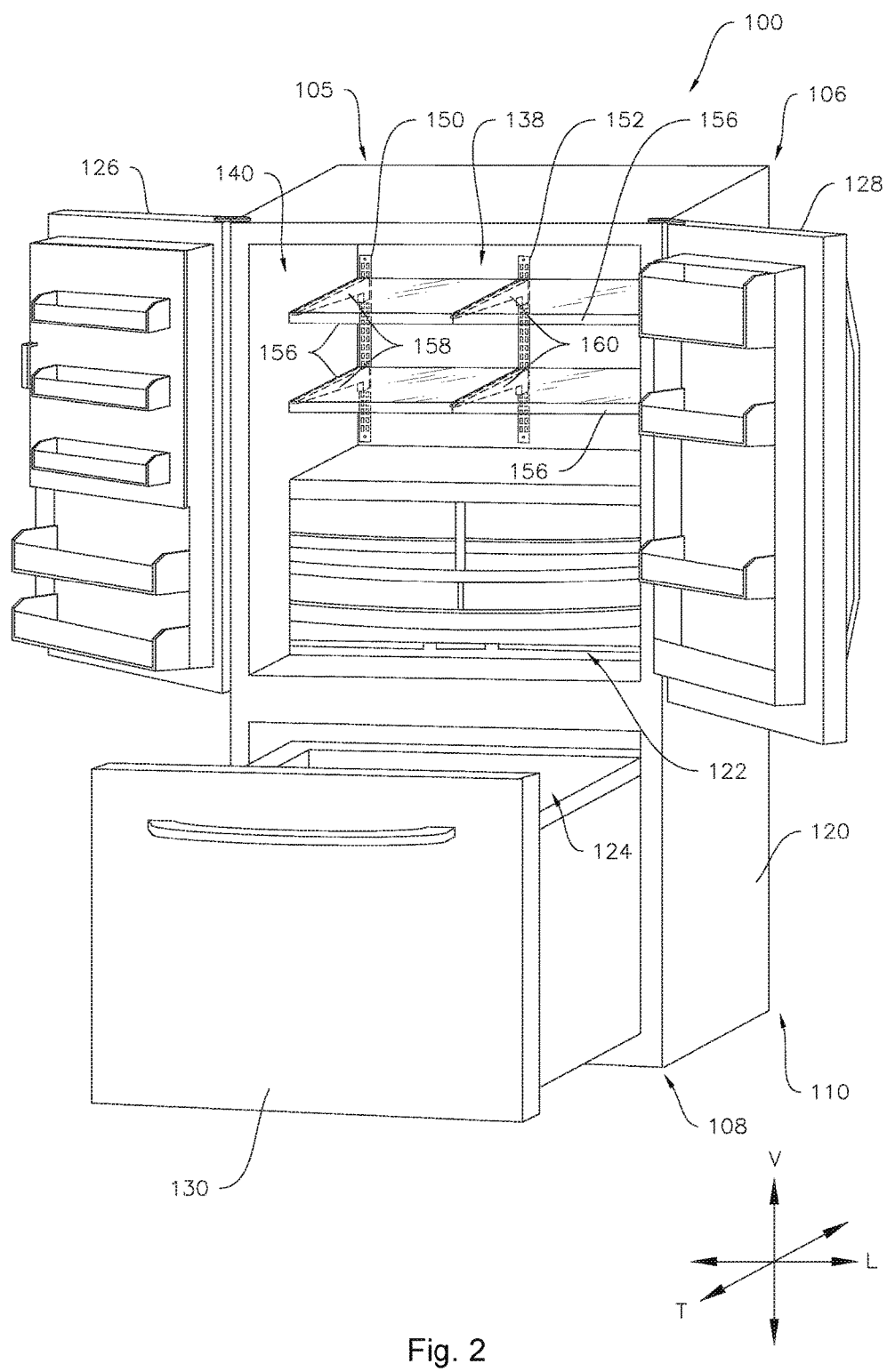
FIG. 2 provides a front perspective view of the refrigerator appliance of FIG. 1 with refrigerator doors and a freezer door shown in an open configuration to reveal a fresh food chamber and freezer chamber of the refrigerator appliance according to an exemplary embodiment of the present subject matter.

FIG. 2 provides a front, perspective view of refrigerator appliance 100 having refrigerator doors 126, 128 in an open position to reveal the interior of fresh food chamber 122. Additionally, freezer door 130 is shown in an open position to reveal the interior of freezer chamber 124. As shown more clearly in FIG. 2, refrigerator appliance 100 extends in the transverse direction T between a front portion 108 and a back portion 110.

Figure 3:
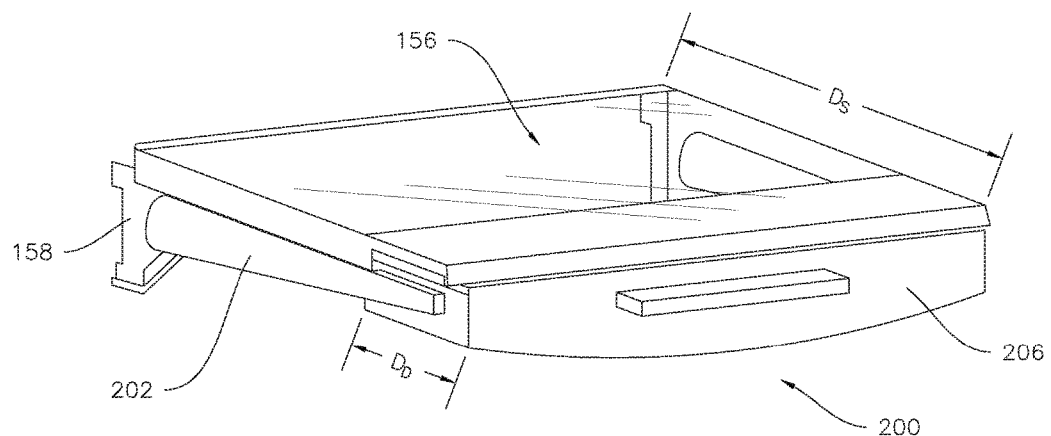
FIG. 3 provides a perspective view of a first position of a drawer assembly removably mounted to a shelf, such as a shelf of the refrigerator appliance of FIG. 1 according to an exemplary embodiment of the present subject matter.

As shown in FIG. 2, for this exemplary embodiment, fresh food chamber 122 of refrigerator appliance 100 includes a first support member 150 and a second support member 152 disposed proximate the back portion 110, e.g., mounted to a rear wall 138 of cabinet 120. The first and second support members 150 and 152 are oriented generally along the vertical direction V. One or more adjustable shelves 156 may be mounted to the first and second support members 150 and 152. First and second support members 150 and 152 structurally support one or more adjustable shelves 156. Moreover, first and second support members 150 and 152 structurally support the weight of other components, e.g., the additional weight from a removably mountable drawer assembly 200 (FIG. 3). First and second support members 150 and 152 can be made of any suitable structural material. For example, in some embodiments, first and second support members 150 and 152 may be made of steel.

In the embodiment illustrated in FIG. 2, four (4) adjustable shelves 156 are mounted within fresh food chamber 122 and are arranged in two columns and two rows as shown. Adjustable shelves 156 may be selectively positioned by a user in different shelf mounting positions within fresh food chamber 122. For instance, one adjustable shelf 156 could be removed from its position and moved upward or downward along the vertical direction V or moved from a position proximate first side 105 to a position proximate second side 106 of refrigerator appliance 100 along the lateral direction L. Adjustable shelves 156 can also be removed from refrigerator appliance 100. For example, if storage room is needed for a particularly tall pot, adjustable shelves 156 can be removed from refrigerator appliance 100 and stowed elsewhere. Although four (4) adjustable shelves 156 are depicted in FIG. 2, more or less than four (4) adjustable shelves 156 can be provided in refrigerator appliance 100.

As shown in FIG. 2, each adjustable shelf 156 may include a first bracket 158 and a second bracket 160 for mounting the shelf 156 to the first and second support members 150 and 152 in one of the shelf mounting positions. For example, the shelf 156 may extend between the first bracket 158 and the second bracket 160 along the lateral direction L. As is generally understood in the art, the first and second support members 150 and 152 may include a plurality of openings and the first and second brackets 158 and 160 may include hooks configured to selectively engage and disengage the openings such that the shelves 156 can be positioned as desired.

Figure 4:
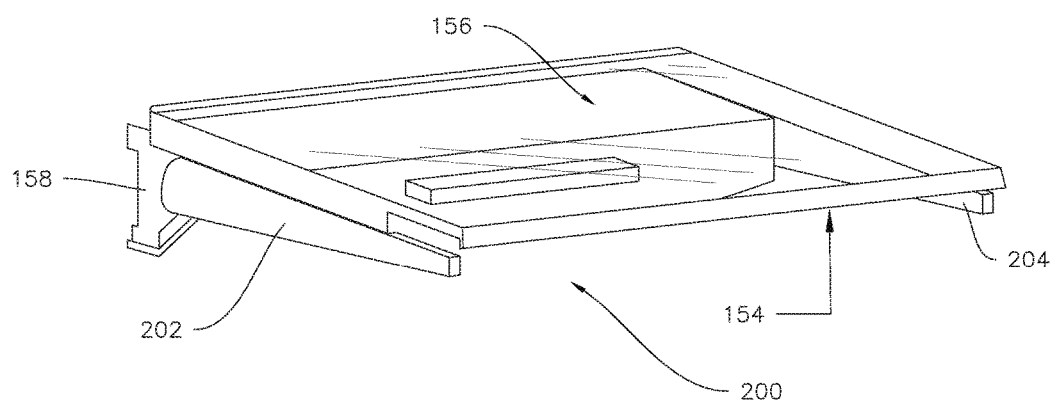
FIG. 4 provides a perspective view of the drawer assembly of FIG. 3 in a second position.

FIGS. 3 and 4 provide perspective views of a drawer assembly 200 removably mounted to shelf 156. As illustrated, the removably mountable drawer assembly 200 includes a first rail 202 and a second rail 204 with a housing 206 therebetween. The rails 202, 204 may be mounted to the housing 206, e.g., with adhesives or fasteners, or may be integrally formed with the housing 206 as a one-piece seamless construction, for example by additive manufacturing. The first rail 202 and the second rail 204 of the drawer assembly 200 are configured for removably mounting to the first bracket 158 and the second bracket 160, respectively, proximate a bottom surface 154 of the shelf 156.

The housing 206 of the removably mountable drawer assembly 200 may be slidable relative to the shelf 156, e.g., along the transverse direction T, on the first rail 202 and the second rail 204. For example, the housing 206 may be able to slide between a forward position as illustrated in FIG. 3 for ease of access to the housing 206 and a back position as illustrated in FIG. 4, such that taller items may be stored below shelf 156 and in front of the housing 206 when desired. Accordingly, the housing 206 of the drawer assembly 200 may be smaller than the shelf 156. For example, the shelf 156 may define a depth $D_S$ along the transverse direction T and the housing 206 of the drawer assembly 200 may define a depth $D_D$ along the transverse direction T, where the depth $D_D$ is less than the depth $D_S$. In some exemplary embodiments, the depth $D_D$ of the housing 206 may be about two-thirds of the depth $D_S$ of the shelf 156. In some exemplary embodiments, the depth $D_D$ of the housing 206 may be about half of the depth $D_S$ of the shelf 156. As used herein, terms of approximation such as "about" include within ten percent more or less than the stated value.

Figure 5:
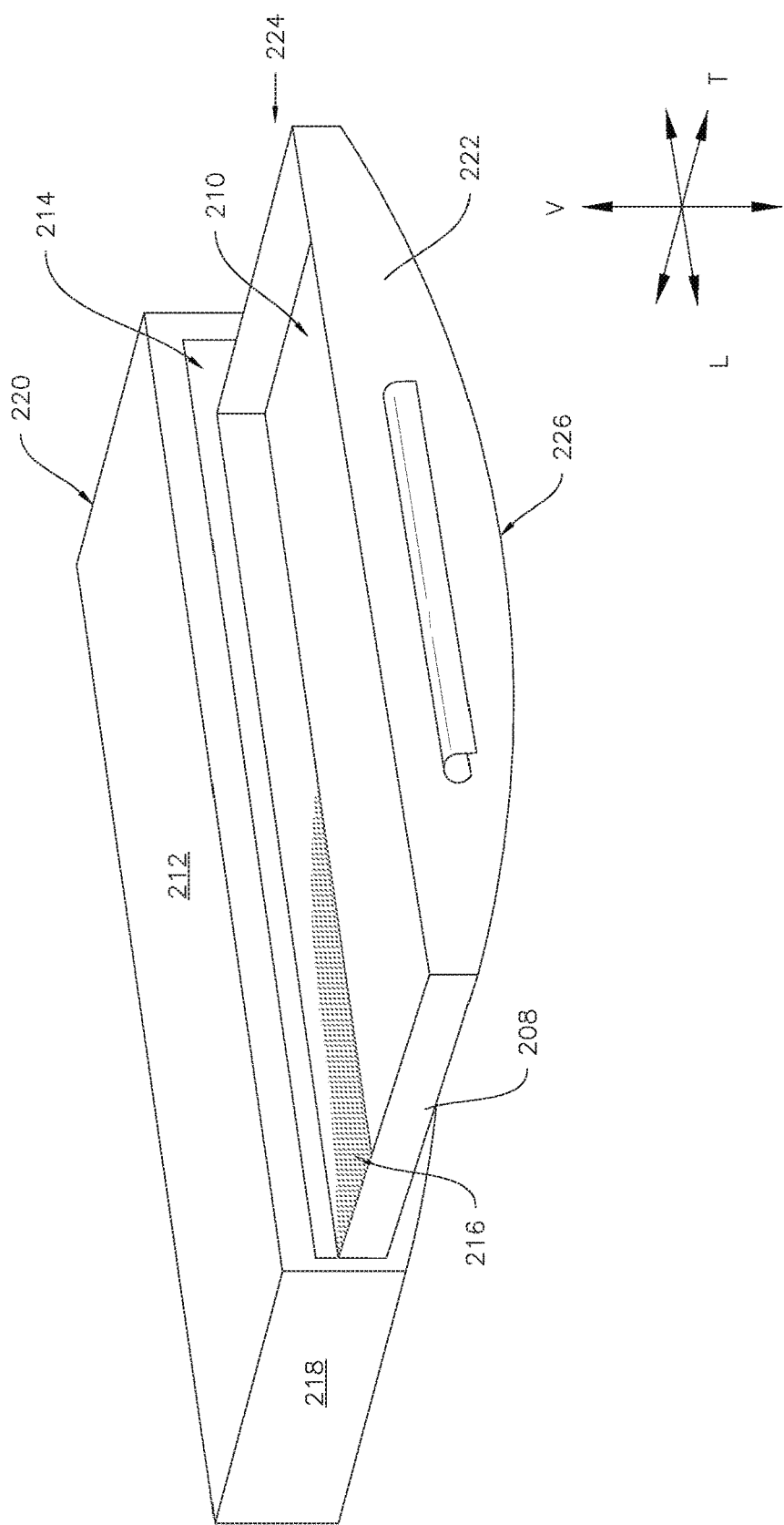
FIG. 5 provides a perspective view of portions of the drawer assembly of FIG. 3.

In some embodiments, such as is illustrated for example in FIG. 5, the housing 206 may extend between a first side 218 and a second side 220 along the lateral direction L, where the second side 220 is opposite the first side 218. The first rail 202 and second rail 204 are not illustrated in FIG. 5 solely for the sake of simplicity and to more clearly illustrate the housing 206. Referring now to FIGS. 4 and 5, the first rail 202 (FIG. 4) may extend along the transverse direction T at the first side 218 (FIG. 5) of the housing 206 and the second rail 204 (FIG. 4) may extend along the transverse direction T at the second side 220 (FIG. 5) of the housing 206.

As illustrated for example in FIG. 5, the housing 206 may include an exterior 212, an interior 214, and a chamber 216 defined in the interior 214. The drawer assembly 200 may further include a drawer 208 slidably mounted within the chamber 216 of the housing 206. As illustrated in FIG. 5, the drawer 208 may define a food storage compartment 210. A door 222 may be positioned at a front portion of the drawer 208 and the door 222 may be configured to sealingly enclose the chamber 216 of the housing 206 when the drawer 208 is in a closed position. Thus, housing 206 and drawer 208 may cooperate to sealingly enclose the chamber 216 of the housing 206 when the drawer 208 is in the closed position. As used herein, the term "sealingly enclose" includes but is not necessarily limited to a fluid-tight seal. Rather, the chamber 216 of the housing 206 may be sealingly enclosed when the drawer 208 is in the closed position so long as the enclosure is sufficiently tight to permit the humidity within the chamber 216 to be relatively higher than the surrounding volume within, e.g., the fresh food chamber 122. For example, the chamber 216 may be sealingly enclosed when over seventy-five percent (75%) of the surface area of the enclosure does not allow significant mass transfer, e.g., between chamber 216 of the housing 206 and the fresh food chamber 122. Such sealing enclosures may advantageously promote extended shelf life of produce stored in chamber 216 based on environmental conditions such as the relatively higher humidity within the chamber 216.

Figure 6:
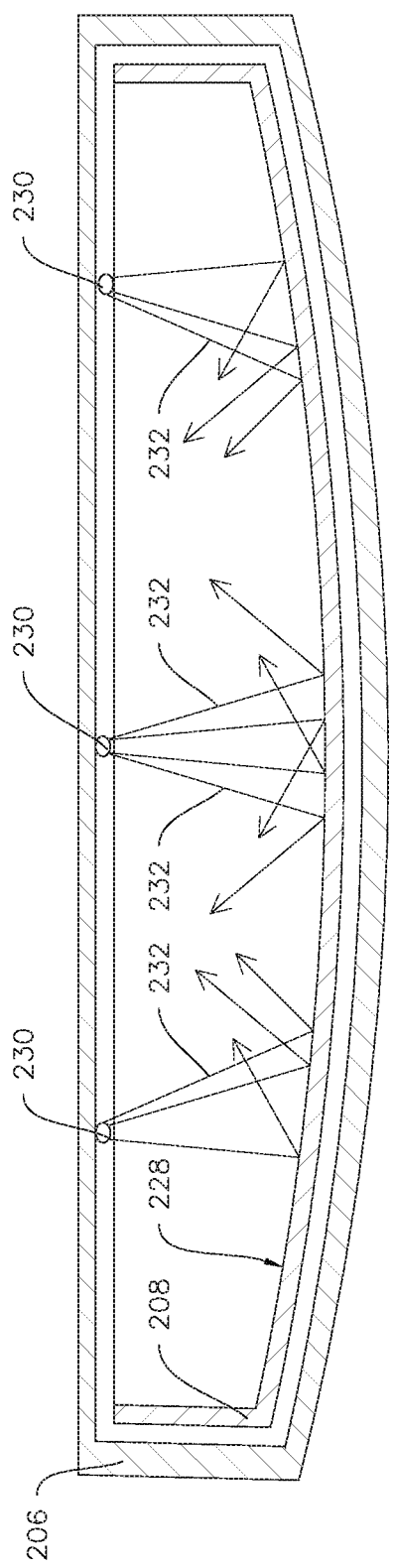
FIG. 6 provides a section view through the portions of the drawer assembly shown in FIG. 5.

As illustrated in FIG. 6, the drawer assembly 200 may further include a plurality of light-emitting diodes 230. FIG. 6 provides a section view through the housing 206 and drawer 208 when the drawer 208 is at least partially in the closed position. As illustrated, the plurality of light-emitting diodes 230 may be positioned in the interior 214 (FIG. 5) of the housing 206. In addition, light-emitting diodes 230 may be positioned on a top wall of housing 206, e.g., such that light-emitting diodes 230 are positioned above food storage compartment 210 along the vertical direction V. In various embodiments, the plurality of light-emitting diodes 230 may be operable to irradiate the food storage compartment 210 (FIG. 5) of the drawer 208 when the drawer 208 is in the closed position. For example, the plurality of light-emitting diodes 230 may be configured to emit ultraviolet (UV) light. For example, in some embodiments, the light-emitting diodes 230 may be configured to emit UV-B light. UV-B light may advantageously provide a closer approximation to natural light to promote freshness of produce items stored in the food storage compartment 210 (FIG. 5). It should be noted that the present disclosure is not necessarily limited to light-emitting diodes 230; any suitable lighting device may be employed.

As may be seen in FIG. 5, the drawer 208 may include a top portion 224 and a bottom portion 226 opposite the top portion 224 along the vertical direction V. The bottom portion 226 may define an arcuate shape positioned at a lowermost portion of the storage compartment 210 within the drawer 208. Thus, a bottom wall of drawer 208 may have an arcuate cross-section, e.g., in a plane that is perpendicular to the transverse direction T. In particular, the bottom wall of drawer 208 may have the arcuate cross-section along the depth $D_D$ of the housing 206. Turning now to FIG. 6, the bottom portion 226 may include a reflective interior surface 228. In such embodiments, the arcuate shape of the bottom portion 226 may be configured to focus the ultraviolet light 232 emitted by the plurality of light-emitting diodes 230 towards the center of the food storage compartment 210 of the drawer 208. Thus, the parabolic geometry of the reflective interior surface 228 may advantageously focus the radiation (e.g., UV light 232) towards the center of the compartment 210, avoiding places where food items are less likely to be located. For example, most fruit and vegetables have at least some rounded aspect to their shape, such that the fruit and/or vegetable items which may be stored within the compartment 210 are likely to roll under the influence of gravity along the arcuate bottom portion 224 towards the center of the compartment 210. As another example, a plurality of smaller berries, e.g., blueberries, may be stored in a box and although the box may not be round, the box of blueberries may also slide under the influence of gravity along the arcuate bottom portion 224 towards the center of the compartment 210.

As noted above, the refrigerator appliance 100 may include a controller 134. The controller 134 may be in operative communication with the plurality of light-emitting diodes 230. In such embodiments, the controller configured to operate the plurality of light-emitting diodes 230 over a twenty-four hour cycle. Such operation of the plurality of light-emitting diodes 230 may advantageously approximate the daily light-dark cycle that produce items stored in the compartment 210 would naturally be exposed too, e.g., prior to harvesting. Accordingly, the circadian rhythm of the produce items may be maintained or supported which may result in prolonged shelf life of the produce items when stored within the compartment 210.

Figure 7:
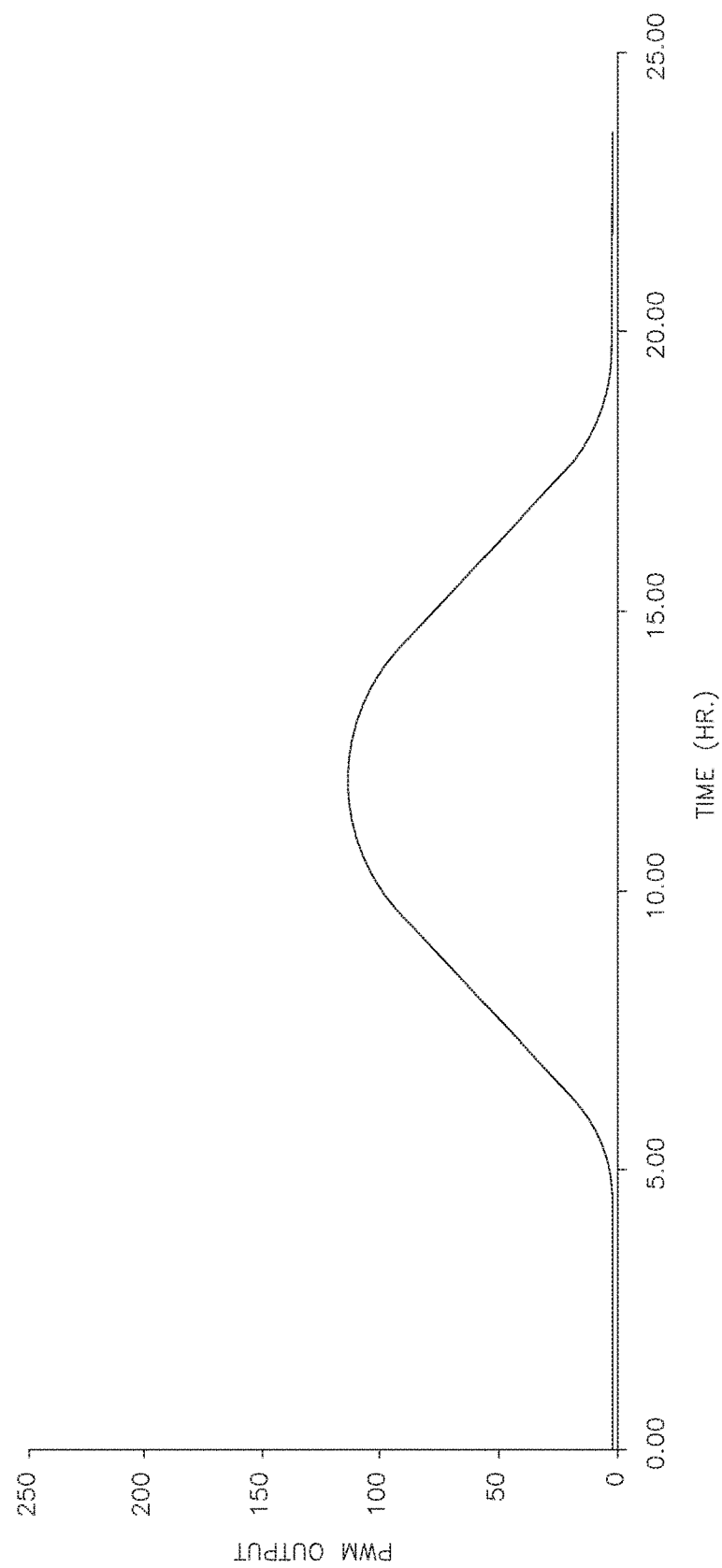
FIG. 7 provides a graph of an exemplary twenty-four hour cycle according to one or more embodiments of the present subject matter.

In some embodiments, the controller 134 may be a pulse-width modulation (PWM) controller configured to operate the plurality of light-emitting diodes 230 over a twenty-four hour cycle, such that the twenty-four hour cycle includes time-varying light intensity to help match the circadian rhythm of produce within the food storage compartment 210 of the drawer 208. An exemplary cycle according to some embodiments is illustrated by the graph in FIG. 7. In some embodiments, the twenty-four hour cycle may include activating the plurality of light-emitting diodes 230 at a first time, e.g., as indicated at about hour five on the horizontal axis in the graph of FIG. 7. The twenty-four hour cycle may also include gradually increasing an intensity of light emitted by the plurality of light-emitting diodes 230 for a first period of time, e.g., as indicated from about hour five to about hour twelve on the horizontal axis in the graph of FIG. 7. Accordingly, produce within the drawer may be irradiated with a gradually increasing intensity of ultraviolet light during the first period of time. Further in some example embodiments, where the controller 134 may be a PWM controller, the output of the PWM controller gradually increases over the first period of time, as indicated along the vertical axis in the graph of FIG. 7. The twenty-four hour cycle may also include gradually decreasing the intensity of light emitted by the plurality of light-emitting diodes 230 for a second period of time, e.g., from about hour twelve to about hour nineteen as illustrated for example in FIG. 7. Accordingly, produce within the drawer may be irradiated with a gradually decreasing intensity of ultraviolet light during the second period of time. The intensity may decrease until the plurality of light-emitting diodes 230 are deactivated, e.g., where the output of controller 134 reaches zero on the example graph of FIG. 7 and, correspondingly, the ultraviolet light is about zero. The twenty-four hour cycle may further include keeping the plurality of light-emitting diodes deactivated, e.g., keeping the intensity of the ultraviolet light at about zero, for a third period of time, e.g., as illustrated in FIG. 7 from about hour nineteen until about hour five of the following day. In various embodiments, the first period of time, the second period of time, and the third period of time may collectively define a twenty-four hour period of the twenty-four hour cycle. For example, in the illustrated embodiment of FIG. 7, the twenty-four hour cycle includes a first period of about seven hours, a second period of about seven hours, and a third period of about ten hours. Further, in some embodiments, the controller 134 may be configured to repeat the twenty-four hour cycle, e.g., such that the first, second and third periods are repeated daily.

In some embodiments, the hours of the twenty-four hour cycle may correspond to the local time, e.g., hour five as described above may correspond to five o'clock AM. Thus, in the example illustrated by FIG. 7, the twenty-four hour cycle may begin at about midnight on a first day and may end at about midnight on a following day. The controller 134 may be configured to receive a local time and to synchronize the twenty-four hour cycle with the local time such that the hours of the twenty-four hour cycle correspond to the local time. For example, the controller 134 may be configured to communicate (e.g. using a wired or wireless connection) with a separate device external to the appliance, such as a communications device. The communications device may be a laptop computer, smartphone, tablet, personal computer, wearable device, smart home system, and/or various other suitable devices. The controller 134 may be in communication with the separate communications device through various possible communication connections and interfaces. For purposes of the description herein, possible wired or wireless communication connections and interfaces can include, but are not limited to, wireless radio, WI-FI®, BLUETOOTH®, ZIGBEE®, laser, infrared, and Ethernet type devices and interfaces. Accordingly, the controller 134 may receive the local time from the separate communications device, e.g., a smart phone, via a wireless connection such as WI-FI®. The local time may be sent to the controller 134 by a user-initiated function, e.g., on the smart phone, or automatically, e.g., the smart phone may include software configured to automatically synchronize with the controller 134. In other embodiments, the local time may be input by a user via the user interface panel 136.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A refrigerator appliance defining a vertical direction, a lateral direction, and a transverse direction, the vertical, lateral, and transverse directions being mutually perpendicular, the refrigerator appliance comprising:

a cabinet defining a food storage chamber, the food storage chamber extending between a top portion and a bottom portion along the vertical direction, a first side portion and a second side portion along the lateral direction, and a front portion and a back portion along the transverse direction;

a first support member and a second support member disposed proximate the back portion of the food storage chamber for providing a plurality of shelf mounting positions;

a shelf having a first bracket and a second bracket attached to the shelf for mounting the shelf to the first and second support members in one of the shelf mounting positions, the shelf having a top surface and a bottom surface; and a removably mountable drawer assembly comprising:

a housing comprising an exterior, an interior, and a chamber defined in the interior of the housing;

a drawer slidably mounted within the chamber of the housing, the drawer defining a food storage compartment;

a door positioned at a front portion of the drawer, the door configured to sealingly enclose the chamber of the housing when the drawer is in a closed position;

a first rail extending along the transverse direction on a first side of the exterior of housing; and a second rail extending along the transverse direction on a second side of the exterior of the housing, the second side opposite the first side;

wherein the first rail is mounted to the first bracket of the shelf proximate to the bottom surface of the shelf and the second rail is mounted to the second bracket of the shelf proximate to the bottom surface of the shelf.

2. The refrigerator appliance of claim 1, further comprising a plurality of light-emitting diodes, the plurality of light-emitting diodes positioned in the interior of the housing of the removably mountable drawer assembly, the plurality of light-emitting diodes operable to irradiate the food storage compartment of the drawer when the drawer is in the closed position.

3. The refrigerator appliance of claim 2, wherein the plurality of light-emitting diodes are configured to emit ultraviolet light.

4. The refrigerator appliance of claim 3, wherein the drawer of the removably mountable drawer assembly comprises a top portion and a bottom portion opposite the top portion along the vertical direction, the bottom portion defining an arcuate shape positioned at a lowermost portion of the storage compartment within the drawer, and the bottom portion comprises a reflective interior surface, the arcuate shape of the bottom portion configured to focus the ultraviolet light emitted by the plurality of light-emitting diodes towards the center of the food storage compartment of the drawer.

5. The refrigerator appliance of claim 2, further comprising a controller in operative communication with the plurality of light-emitting diodes, the controller configured to operate the plurality of light-emitting diodes over a twenty-four hour cycle, the twenty four hour cycle comprising: activating the plurality of light-emitting diodes at a first time, gradually increasing an intensity of light emitted by the plurality of light-emitting diodes for a first period of time, gradually decreasing the intensity of light emitted by the plurality of light-emitting diodes for a second period of time until the plurality of light-emitting diodes are deactivated, and keeping the plurality of light-emitting diodes deactivated for a third period of time, wherein the first period of time, the second period of time, and the third period of time collectively define a twenty-four hour period.

6. The refrigerator appliance of claim 1, wherein the housing of the removably mountable drawer assembly is slidable relative to the shelf along the first rail and the second rail.

7. The refrigerator appliance of claim 1, wherein the housing of the removably mountable drawer assembly defines a depth along the transverse direction, the shelf defines a depth along the transverse direction, and the depth of the housing is two-thirds of the depth of the shelf.

8. The refrigerator appliance of claim 1, wherein the housing of the removably mountable drawer assembly defines a depth along the transverse direction, the shelf defines a depth along the transverse direction, and the depth of the housing is half of the depth of the shelf.

9. A removably mountable drawer assembly for a refrigerator, the drawer assembly comprising:

a housing defining a vertical direction, a lateral direction, and a transverse direction, the vertical, lateral, and transverse directions being mutually perpendicular, the housing comprising an exterior, an interior, and a chamber defined in the interior of the housing;

a drawer slidably mounted within the chamber of the housing, the drawer defining a food storage compartment;

a door positioned at a front portion of the drawer, the door configured to sealingly enclose the chamber of the housing when the drawer is in a closed position;

a first rail extending along the transverse direction on a first side of the exterior of housing; and a second rail extending along the transverse direction on a second side of the exterior of the housing, the second side opposite the first side, the first rail and the second rail removably mounted to a first bracket and a second bracket of a shelf proximate a bottom surface of the shelf.

10. The drawer assembly of claim 9, further comprising a plurality of light-emitting diodes, the plurality of light-emitting diodes positioned in the interior of the housing, the plurality of light-emitting diodes operable to irradiate the food storage compartment of the drawer when the drawer is in the closed position.

11. The drawer assembly of claim 10, wherein the plurality of light-emitting diodes are configured to emit ultraviolet light.

12. The drawer assembly of claim 11, wherein the drawer comprises a top portion and a bottom portion opposite the top portion along the vertical direction, the bottom portion defining an arcuate shape, and the bottom portion comprises a reflective interior surface, the arcuate shape of the bottom portion configured to focus the ultraviolet light emitted by the plurality of light-emitting diodes towards the center of the food storage compartment of the drawer.

13. The drawer assembly of claim 10, further comprising a controller in operative communication with the plurality of light-emitting diodes, the controller configured to operate the plurality of light-emitting diodes over a twenty-four hour cycle, the twenty four hour cycle comprising: activating the plurality of light-emitting diodes at a first time, gradually increasing an intensity of light emitted by the plurality of light-emitting diodes for a first period of time, gradually decreasing the intensity of light emitted by the plurality of light-emitting diodes for a second period of time until the plurality of light-emitting diodes are deactivated, and keeping the plurality of light-emitting diodes deactivated for a third period of time, wherein the first period of time, the second period of time, and the third period of time collectively define a twenty-four hour period.

14. The drawer assembly of claim 9, wherein the housing is slidable relative to the shelf along the first rail and the second rail.

15. The drawer assembly of claim 9, wherein the housing defines a depth along the transverse direction, the shelf defines a depth along the transverse direction, and the depth of the housing is two-thirds of the depth of the shelf.

16. The drawer assembly of claim 9, wherein the housing defines a depth along the transverse direction, the shelf defines a depth along the transverse direction, and the depth of the housing is half of the depth of the shelf.

17. A method of extending the shelf life of produce stored in a drawer of a refrigerator, the method comprising:

operating a plurality of light-emitting diodes over a twenty-four hour cycle, the twenty-four hour cycle comprising:
  irradiating the produce within the drawer with a gradually increasing intensity of ultraviolet light for a first period of time;
  irradiating the produce within the drawer with a gradually decreasing intensity of ultraviolet light for a second period of time until the intensity of the ultraviolet light is about zero; and
  keeping the intensity of the ultraviolet light at about zero for a third period of time;
  wherein the first period of time, the second period of time, and the third period of time collectively define a twenty-four hour period; and
repeating the twenty-four hour cycle.

18. The method of claim 17, further comprising synchronizing the twenty-four hour cycle with a local time.

19. The method of claim 17, wherein the first period of time comprises about seven hours and the second period of time comprises about seven hours.

\* \* \* \* \*